United States Patent [19]
Sieber

[11] 3,930,983
[45] Jan. 6, 1975

[54] ARRANGEMENT AND PROCESS FOR DETERMINING ANTIGENS

[75] Inventor: Axel Sieber, Marburg, Marbach, Germany

[73] Assignee: Behringwerke Aktiengesellschaft, Marburg an der Lahn, Germany

[22] Filed: Feb. 12, 1975

[21] Appl. No.: 549,431

[30] Foreign Application Priority Data
Feb. 14, 1974 Germany............................ 2406959

[52] U.S. Cl. .......... 204/299; 204/180 G; 204/180 S
[51] Int. Cl.² ........................................ B01K 5/00
[58] Field of Search ............ 204/180 S, 180 G, 299

[56] References Cited
UNITED STATES PATENTS

| | | |
|---|---|---|
| 3,432,424 | 3/1969 | Zec ..................................... 204/299 |
| 3,554,894 | 1/1971 | Zemel................................. 204/299 |
| 3,558,459 | 1/1971 | Granstrand et al............. 204/180 G |
| 3,582,490 | 6/1971 | Zemel............................ 204/180 G |
| 3,674,678 | 7/1972 | Post, Jr. et al...................... 204/299 |

*Primary Examiner*—John H. Mack
*Assistant Examiner*—A. C. Prescott
*Attorney, Agent, or Firm*—Curtis, Morris & Safford

[57] ABSTRACT

An arrangement for the simultaneous qualitative or quantitative determination of several antigens in mixtures of antigens by immunoelectrophoresis in a matrix containing antibodies, by coating the support for the matrix with several matrix strips, one following the other and each containing a specific antiserum, and a process for the determination of several antigens in mixtures, wherein said arrangement is used.

4 Claims, 2 Drawing Figures

U.S. Patent  Jan. 6, 1976  3,930,983
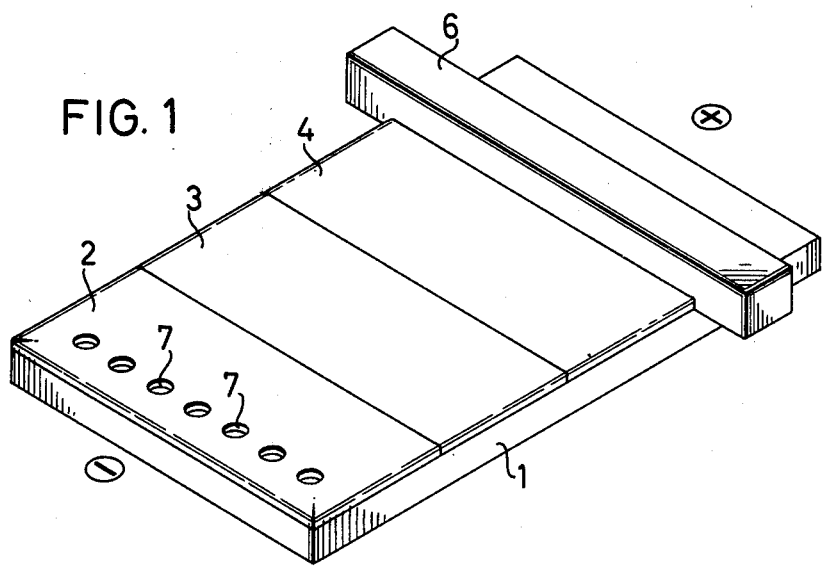
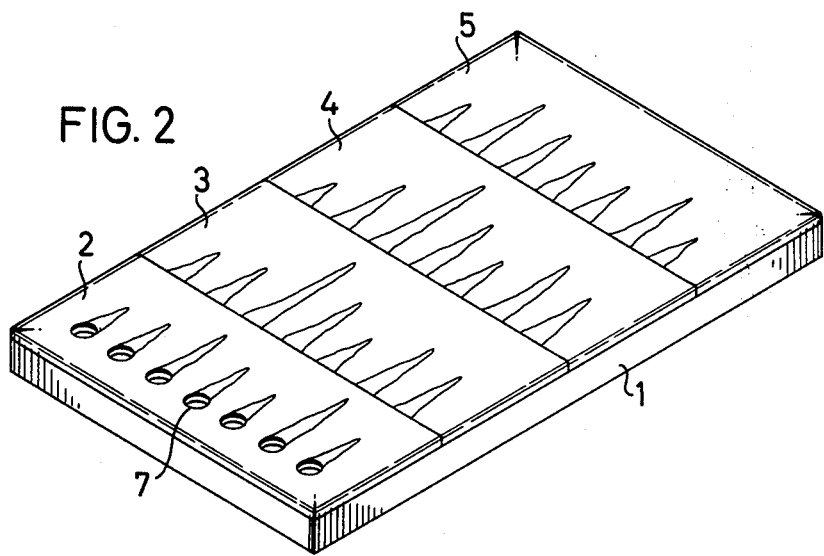

ARRANGEMENT AND PROCESS FOR DETERMINING ANTIGENS

The present invention relates to an arrangement for the simultaneous qualitative or quantitative immunological determination of several antigens and to a process for using it.

Human serum and body fluids contain protein species which can be referred to in medicinal diagnostics under a collective name according to certain clinical pictures or physiological tasks. For example, the proteins acid $\alpha_1$-glycoprotein, $\alpha_1$-antitrypsin, coeruloplasmin and haptoglobin, which change during inflammatory diseases with regard to the normal values, are referred to as acute-phase proteins. The term immunoglobulins comprises the proteins IgG, IgA, IgM, IgD and IgE. They substantially influence the immunization of the organism, and their concentrations undergo characteristical changes due to certain diseases.

In the quantitative protein analysis, it is therefore necessary to examine several proteins of such a group for a diagnosis or the determination of a clinical picture. It can be expected that an increasing number of these protein groups will be found which, due to certain clinical pictures, undergo changes in concentration that have to be correlated.

Therefore, in series tests on patients who suffer from acute inflammatory diseases, it is desirable that the concentration values, for example of four acute-phase proteins, can be determined in a single analysis. It has been necessary up to now to carry out one analysis for each species of proteins.

Immunological evidence and determination is based on the property of antigens to react with antibodies, which are contained in corresponding antisera and have a specific action against these antigens, in stoichiometric amounts, while forming precipitates. The methods, referred to as simple linear and simple radial immune diffusion, are based on the fact that antigens diffuse into a matrix containing an antiserum and thereby form an antigen/antibody complex. The equivalence range of complex formation corresponds to the concentration of the reactants and is indicated by the outlines of a precipitate, which can be observed with the naked eye or made visible by coloring them with adequate dyes.

When an antigen is moved through an electric field in a matrix containing a homologue antibody, a more or less stretched-out precipitate is formed as a function of the migration velocity of the antigen. The diffusion or migration distance in each case is taken as a measure for the amount of the antigen to be determined. If there is no relation with a standard amount, the formation of a precipitate is taken as qualitative evidence for the unknown substance.

These techniques called immuno-diffusion or immuno-electrophoresis, however, permit the determination of only one single antigen per analysis. Further development of the immuno-electrophoresis has been disclosed by Laurell, Scand. J. clin. Lab. Invest. 29, suppl. 124, pages 21–37 (1972), which generally permits the determination of several antigens by electro-immuno-diffusion using an antiserum that contains antibodies with specific action against several antigens. For a mixture of two antibody species, that method still provides relatively discernable pictures. The length of the immunization precipitates, however, depends on the protein concentration, so it is not easy to decide which of the precipitate peaks building up from the same starting spot is to be attributed to a determined protein. Things become a complete mess if more than two species of antibodies are applied.

Hence, the essential limit to that method is that, on the one hand, the amount of concentration and the electrophoretic behavior of the two antigens have to provide precipitates which differ from each other and, on the other hand, it must be easily possible to decide which precipitate is to be attributed to each individual antigen to be determined. Otherwise, fatal misinterpretation of results may occur in the examination of patients' sera. Moreover, ambiguous results require a repeated determination, for which adequate material is no longer available in many cases.

There has long been demand for an immunological method of determining several antigens of one sample in a single operation, which excludes confusion of the concentrations established.

As mentioned, it has been known to determine the corresponding antigen in a mixture of antigens by subjecting it to an electrophoresis in a matrix containing a monospecific antibody against one of the antigens.

Surprisingly, it has now been found that in the electrophoretic migration of a mixture of antigens through several matric strips put in series, each strip containing a specific antiserum against a single antigen, each individual matrix strip behaved as if the electrophoresis had been carried out using a matrix that had uniformly be charged with only one antibody. The antigens migrate unattacked through the matrix strips containing an antiserum other than that specific for them and precipitate exclusively in the matrix strip containing the antiserum which is specific for them. In this manner, the qualitative or quantitative determination of several antigens at the same time is possible.

Object of this invention is therefore an arrangement for the simultaneous qualitative or quantitative determination of several antigens in antigen mixtures by immuno-electrophoresis in a matrix containing antibodies, which arrangement is characterized in that a support for the matrix is coated with several matrix strips, one placed next to the other and each containing a specific antiserum.

Further object of the invention is a process for the qualitative or quantitative determination of antigens by using this arrangement.

Immuno-electrophoresis is most frequently performed on agar or agarose gel as the matrix. Other gel-forming substances, such as starch, gelatin or acrylamide may, however, also be used.

The arrangement of the invention is illustrated diagrammatically by way of example in the accompanying drawing. In the drawing, FIG. 1 is a perspective view of the arrangement during preparation. FIG. 2 is a perspective view of the arrangement with the typical distribution of the precipitates on the matrix during immuno-electrophoresis.

In FIG. 1, a support plate 1 is being coated with agar as a matrix in gel strips 2 to 5, each strip containing a determined monospecific antiserum. The strips are produced successively in a desired width by spreading a liquid solution that contains the antiserum and consists for example of agar or agarose in an electrophoresis buffer on a horizontal plate while limiting the area of the plate, which is to be coated with a gel strip, for example by means of a bar 6, preferably made of metal.

After the gel has solidified, this bar is moved further and the next strip is produced by filling liquid gel in the space thus freed. In an advantageous dimension, the gel strips have a width of about 2 to 4 cm. Thus, up to four or five different gel strips can be placed on a usual plate sized 10 × 10 cm. The lowermost gel strip 2 (cathode), labeled −, should contain the antiserum against the antigen having the lowest migration velocity in the electric field, the uppermost strip 5 (anode, not yet placed in FIG. 1) and labeled + contains the antiserum against the antigen having the highest migration velocity. The lowermost strips are then punched to provide holes 7, which are filled with the antigen solutions to be examined. Thus, the plate illustrated in FIG. 1 is suitable for determining four different species of antigens in seven samples. An accordingly increased number of samples can be applied using correspondingly longer support plates and adequate equipment.

The matrix strips may, however, also be arranged in such a manner that the holes (application points) are placed in a small strip of antiserum-free gel, followed by the first strip of gel that contains the antiserum. This arrangement has the advantage that the antigens enter the first gel strip successively according to their migration velocity. Thus, the slowest antigen reacting in the first strip does not hamper the rest of the antigens, while forming the immunization precipitate, since these have already migrated farther.

The electrophoretical separation is carried out under the usual conditions of electro-immuno-diffusion in an adequate apparatus. The antigens are introduced as solutions into the application holes by means of a micro-pipette or a microliter syringe. After an electric field of 7 to 10 V/cm has been established, the antigens migrate undisturbed through the antiserum-containing gel strips until inhibited by the antibodies having a specific activity against them in the corresponding strip.

After an electrophoresis time of about 3 hours, the reaction is complete. In a low-voltage field, for example of 2–3 V/cm, the electrophoresis takes 8 to 16 hours. The reaction proceeds with the formation of rocket-shaped immunization precipitates, the length of which is a measure for the concentration of antigens. Upon electrophoresis, the antigen/antibody complex is advantageously colored by means of appropriate dyes, for example with the dyestuff Coomassi Brilliant Blue R, according to known methods. The precipitate line may be measured by means of a millimeter rule.

In FIG. 2, four antigens are simultaneously determined in seven samples upon electrophoresis and subsequent coloration of the precipitates formed. Application holes 7 correspond to those illustrated in FIG. 1.

The evaluation is made in the usual manner by means of calibrated curves.

A reference curve can be drawn by preparing three or four different dilutions of an adequate antigen standard with a physiological sodium chloride solution as the dilution liquid. These dilutions have to be adjusted so as to cover the preferred measuring range, in the case of plasma proteins, for example 3–30 mg/100 ml. The sera of patients to be examined are advantageously applied in a dilution of 1:2.

An almost straight-lined curve is obtained by transferring the lengths of the precipitates as a function of the standard antigen concentration on graph paper (graded in millimeters).

When a quantitative reference of the antigens to be determined is not needed, the arrangement of the invention is to be used for the qualitative evidence of antigens. This only requires checking if there is a formation of precipitates of the antigen to be determined with the antibody correspondingly applied in the matrix, or not.

The determination may be performed on any antigens which show electrophoretic migration under adequate conditions and against which specific antisera can be obtained. Antigens which, under the conditions chosen, do not show or show only slight electrophoric mobility as such, may be correspondingly modified according to known methods, such as by carbamylation or reaction with β-propiolactone, formaldehyde, ethylene oxide and the like, and may be subjected to the determination method of the invention. A preferred application field of this method is, of course, the clinical diagnosis for the evidence or determination of the constituents of plasma and of body fluids. There is, however, no reason against the arrangement and process also being used for determining microbial metabolic products or vegetable components, provided they show antigen properties.

A plain attribution of the precipitates to the antigens to be determined makes it possible even for persons without special qualification to handle the method of the invention. It will therefore be possible to introduce it with good success as a routine method for clinics and research laboratories.

The following Example illustrates the invention.

EXAMPLE

A matrix layer was prepared by heating a mixture of 1.5 g of agarose and 100 ml of a barbital buffer solution, pH 8.6, $\mu$ 0.02, to the boiling point. After having been clarified, the solution was allowed to cool. Antiserum was admixed at 56°C for preparing the antiserum-containing matrix. The hot liquid agarose solution was cooled in a water bath of 56°C to this temperature which was optimum for the mixture. This bath served at the same time for preheating the antiserum.

The 1.5% agarose solution of 56°C was poured on one end of a glass plate, 10 × 10 cm in size, with the help of a metal bar in a strip of 2 cm width, which did not contain the antiserum. The layer thickness of this agarose strip was about 1.5 mm. About 3 ml of agarose solution were required. After solidification of the gel strip, the metal bar was displaced for 2 cm and the free space was filled out with 3 ml of an agarose gel containing 2% of an anti-C3-serum of rabbits. In the same manner, further strips each with 2% of antitransferrin, 5% of anti-β-lipoprotein and 7% of anti-haptoglobin serum were produced. The antiserum-free strip was punched to provide holes of a diameter of 2.5 mm, which served for receiving 5 $\mu$l each of the patients' sera to be examined.

After the sera had been placed in the holes, the electrophoretic separation was carried out at a field potential of 10 V/cm for 3 hours.

The length of the precipitates obtained was correlated with the corresponding values obtained from standard substances, thus allowing the quantitative determination of the complement factor C 3, of transferrin, of β-lipoprotein and of haptoglobin in a single operation.

I claim:

1. An arrangement for the simultaneous qualitative or quantitative determination of several antigens in mixtures of antigens by immuno-electrophoresis in a matrix containing antibodies, which arrangement comprises coating the support for the matrix with several matrix strips, one following the other and each containing a specific antiserum.

2. An arrangement as claimed in claim 1, wherein the support for the matrix is coated with an antiserum-free matrix strip suitable for receiving the mixtures of antigens, followed by several other matrix strips each containing a specific antiserum.

3. A process for the simultaneous qualitative or quantitative determination of several antigens, which comprises using an arrangement as claimed in claim 1.

4. A process for the simultaneous qualitative or quantitative determination of several antigens, which comprises using an arrangemetn as claimed in claim 2.

* * * * *

UNITED STATES PATENT AND TRADEMARK OFFICE
CERTIFICATE OF CORRECTION

PATENT NO. : 3,930,983
DATED : January 6, 1976
INVENTOR(S) : Axel Sieber

It is certified that error appears in the above-identified patent and that said Letters Patent are hereby corrected as shown below:

In Item [45] of the Heading, correct the issue date to read -- January 6, 1976 --.

Signed and Sealed this twenty-third Day of March 1976

[SEAL]

Attest:

RUTH C. MASON
*Attesting Officer*

C. MARSHALL DANN
*Commissioner of Patents and Trademarks*